(12) United States Patent
Komata et al.

(10) Patent No.: US 6,392,101 B2
(45) Date of Patent: May 21, 2002

(54) PROCESS FOR PURIFYING 1,1,1,5,5,5-HEXAFLUOROACETYLACETONE

(75) Inventors: Takeo Komata; Nariaki Ii; Yoshiki Hirotsu, all of Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/741,092

(22) Filed: Dec. 21, 2000

(30) Foreign Application Priority Data

Jan. 5, 2000 (JP) ........................................ 2000-000526

(51) Int. Cl.⁷ ........................ C07C 45/00; C07C 49/12; B01D 21/01
(52) U.S. Cl. .................. 568/411; 568/366; 568/410; 568/412; 568/407; 210/729
(58) Field of Search ................................ 568/411, 410, 568/412, 366, 407; 210/729

(56) References Cited

PUBLICATIONS

Gilman et al., "Organic Compounds of Uranium. I. 1,3–Dicarbonyl Chelates", J. Am. Chem. Soc., vol. 78 (1956), pp. 2790–2792.

Henne et al., "The Alkaline Condensation of Fluorinated Esters With Esters and Ketones", J. Am. Chem. Soc., vol. 69 (1947), pp. 1819–1820.

Haszeldine et al., "Organic Fluorides. Part VII. Co–ordination Compounds of Fluoroacetylacetones", J. Chem. Soc. of London (1951), pp. 609–612.

Belford et al., "Influence of Fluorine Substitution on the Properties of Metal Chelate Compounds–I", J. Inorganic and Nuclear Chemistry, vol. 2 (1956), pp. 11–31.

*Primary Examiner*—Samuel Barts
*Assistant Examiner*—Eluis O. Prize
(74) *Attorney, Agent, or Firm*—Crowell & Moring LLP

(57) ABSTRACT

The invention relates to a process for purifying a crude 1,1,1,5,5,5-hexafluoroacetylacetone dihydrate containing an impurity. The process includes bringing the crude 1,1,1,5,5,5-hexafluoroacetylacetone dihydrate into contact with a poor solvent in which 1,1,1,5,5,5-hexafluoroacetylacetone dihydrate is substantially insoluble, thereby removing the impurity from the crude 1,1,1,5,5,5-hexafluoroacetylacetone dihydrate. Alternatively, the process includes precipitating crystals of 1,1,1,5,5,5-hexafluoroacetylacetone dihydrate from a solution of the crude 1,1,1,5,5,5-hexafluoroacetylacetone dihydrate. Thus, it is possible to produce 1,1,1,5,5,5-hexafluoroacetylacetone dihydrate of high purity. This product makes it easy to produce 1,1,1,5,5,5-hexafluoroacetylacetone of high purity.

20 Claims, No Drawings

PROCESS FOR PURIFYING 1,1,1,5,5,5-HEXAFLUOROACETYLACETONE

BACKGROUND OF THE INVENTION

The present invention relates to a process for producing 1,1,1,5,5,5-hexafluoroacetylacetone with high purity, which is useful as a raw material for producing medicines, agricultural chemicals and low-boiling-point chelate compounds used in the process for manufacturing electric parts.

H. Gilman et al., J. Am. Chem. Soc., Vol. 78, pp. 2790–2792 (1956) teaches a process for producing 1,1,1 5,5,5-hexafluoroacetylacetone, which is shown by the following reaction formulas:

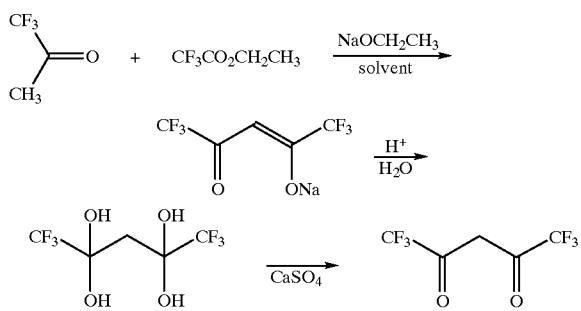

A. Henne et al., J. Amer. Chem. Soc., Vol. 69, pp. 1819–1820 (1947) discloses a process for producing anhydrous 1,1,1,5,5,5-hexafluoroacetylacetone by turning a sodium salt of 1,1,1,5,5,5-hexafluoroacetylacetone into a copper chelate compound, then recrystallizing the copper chelate compound, and then removing the copper with hydrogen sulfide.

R. Haszeldine et al., J. Chem. Soc. London, 1951, pp. 609–612 discloses that a reaction liquid is treated with dilute sulfuric acid and then extracted with ether, and the resulting organic layer is distilled to obtain distillates over the range 36–90° C. It is disclosed therein that the portion of boiling point 85–90° C. appears to be 1,1,1,5,5,5-hexafluoroacetylacetone dihydrate.

H. Gilman et al., J. Am. Chem. Soc., Vol. 78, pp. 2790–2792 (1956) further discloses the precipitation of 1,1,1,5,5,5-hexafluoroacetylacetone dihydrate by concentrating an organic layer extracted with ether.

In general, raw materials, including 1,1,1,5,5,5-hexafluoroacetylacetone, for producing medicines, agricultural chemicals and electronic parts are required to have higher purity, as compared with raw materials for other uses.

SUMMARY OF THE INVENTION

It is therefore an object of the present invention to provide a process for producing 1,1,1,5,5,5-hexafluoroacetylacetone dihydrate with high purity, which is an intermediate for 1,1,1,5,5,5-hexafluoroacetylacetone.

According to the present invention, there is provided a first process for purifying a crude 1,1,1,5,5,5-hexafluoroacetylacetone dihydrate containing an impurity. The first process comprises bringing said crude 1,1,1,5,5,5-hexafluoroacetylacetone dihydrate into contact with a poor solvent, thereby removing said impurity from said crude 1,1,1,5,5,5-hexafluoroacetylacetone dihydrate. In the specification, "poor solvent" means an organic solvent in which 1,1,1,5,5,5-hexafluoroacetylacetone dihydrate is substantially insoluble.

According to the present invention, there is provided a second process for purifying a crude 1,1,1,5,5,5-hexafluoroacetylacetone dihydrate containing an impurity. The second process comprises precipitating crystals of 1,1,1,5,5,5-hexafluoroacetylacetone dihydrate from a specific solution of said crude 1,1,1,5,5,5-hexafluoroacetylacetone dihydrate.

DESCRIPTION OF THE PREFERRED EMBODIMENTS

The process for producing a crude 1,1,1,5,5,5-hexafluoroacetylacetone dihydrate, which is to be purified by the first or second process of the invention, is not particularly limited. For example, such crude 1,1,1,5,5,5-hexafluoroacetylacetone dihydrate can be produced, as follows. At first, a reaction vessel is charged with a reaction solvent and a base. Then, a mixture of 1,1,1-trifluoroacetone, a trifluoroacetic acid ester and a solvent is gradually added to the reaction vessel with stirring or the like to homogenize the reaction mixture, while the reaction mixture was maintained at a predetermined temperature lower than the reaction temperature. Then, according to need, the temperature of the reaction vessel is raised to accelerate the reaction, thereby forming a salt of 1,1,1,5,5,5-hexafluoroacetylacetone.

In the process for producing a crude 1,1,1,5,5,5-hexafluoroacetylacetone dihydrate, the reaction vessel may be made of glass, fluororesin or a material lined with one of these. The reaction solvent may be an ether having a boiling point preferably of about 30–140° C. Examples of such ether are diethyl ether, dibutyl ether, t-butyl methyl ether, diisopropyl ether, and tetrahydrofuran (THF). The base may be an inorganic base. Examples of this inorganic base are alkali metals and alkali earth metals, alkoxides of such metals, and hydrides of such metals. More concrete examples are sodium methoxide, sodium ethoxide, sodium hydride, sodium, potassium methoxide, potassium ethoxide, potassium hydride, potassium, and lithium hydride. The trifluoroacetic acid ester is not particularly limited, since its ester moiety acts as a leaving group. Its examples may be methyltrifluoroacetate and ethyltrifluoroacetate, which are easily available in an industrial scale. The solvent for dissolving 1,1,1-trifluoroacetone and the trifluoroacetic acid ester may or may not be the same ether as that for the reaction solvent. As mentioned above, a mixture of 1,1,1-trifluoroacetone, a trifluoroacetic acid ester, and a solvent may be added to the reaction vessel, in view of operability of the reaction. It is, however, not necessary to mix these components to be added to the reaction vessel. Furthermore, this solvent may be omitted. As mentioned above, it is preferable to cool the reaction mixture during the addition of these components in order to prevent the temperature increase. The reaction temperature is preferably about 0–90° C., more preferably about 20–70° C. If it is lower than 0° C., the reaction rate may become too low. If it is higher than 90° C., the yield of 1,1,1,5,5,5-hexafluoroacetylacetone dihydrate may become too low.

After the completion of the above reaction, a salt of crude 1,1,1,5,5,5-hexafluoroacetylacetone is obtained by removing the reaction solvent. The removal of the reaction solvent is conducted by applying heat and/or vacuum. After that, the reaction liquid of the residue is put into another reaction vessel, followed by the addition of water and then acid (e.g., sulfuric acid, hydrochloric acid, or nitric acid), thereby decomposing the salt. Then, solvent extraction is conducted by adding a solvent to the reaction liquid. Then, the solvent is removed from the obtained organic layer, thereby obtaining a crude 1,1,1,5,5,5-hexafluoroacetylacetone dihydrate containing impurities, in the form of solid.

In the first process, the manner of bringing the crude 1,1,1,5,5,5-hexafluoroacetylacetone dihydrate into contact with a poor solvent is not particularly limited. For example, the crude 1,1,1,5,5,5-hexafluoroacetylacetone dihydrate may be dispersed in the poor solvent. Then, the precipitated 1,1,1,5,5,5-hexafluoroacetylacetone dihydrate can be separated by filtration. As another example, it is possible to apply the poor solvent as a washing liquid to the crude 1,1,1,5,5,5-hexafluoroacetylacetone dihydrate supported on a filter of a filtration device. The resulting 1,1,1,5,5,5-hexafluoroacetylacetone dihydrate is usually dried. However, if it is used as a raw material for producing 1,1,1,5,5,5-hexafluoroacetylacetone, the drying is not necessary.

In the second process, it is possible to dissolve the crude 1,1,1,5,5,5-hexafluoroacetylacetone dihydrate in an organic solvent to form a solution. To this solution it is possible to add a poor solvent, thereby precipitating 1,1,1,5,5,5-hexafluoroacetylacetone dihydrate. Then, this product can be separated by filtration. Alternatively, the above solution can be cooled to reduce solubility, thereby precipitating 1,1,1,5,5,5-hexafluoroacetylacetone dihydrate.

The temperature for conducting the above-mentioned procedures is not particularly limited. It is preferably about 0–90° C., more preferably about 20–60° C. In view of operability, it is preferably a temperature requiring no heating nor cooling.

The above-mentioned poor solvent used in the first or second process can be selected from hydrocarbons and fluorine-containing solvents free from chlorine. It is needless to say that this poor solvent is in the form of liquid upon its use. This poor solvent is not particularly limited, and its boiling point is preferably not higher than about 200° C. Examples of the hydrocarbons are (1) aliphatic hydrocarbons such as n-pentane, n-hexane, n-heptane, n-octane, n-nonane, n-decane and isomers of these, the isomers being in liquid at about 5° C.; (2) aromatic hydrocarbons such as benzene, toluene, o-xylene, m-xylene, p-xylene, ethyl benzene, and mesitylene; (3) alicyclic hydrocarbons such as cyclopentane, cyclohexane, methylcyclopentane, methylcyclohexane, tetralin, and decalin; and (4) industrial gasolines (mixtures of hydrocarbon solvents) such as ligroin and petroleum ether. Examples of the fluorine-containing solvents are 1,2-bis(trifluoromethyl)benzene, 1,3-bis (trifluoromethyl)benzene, 1,4-bis (trifluoromethyl)benzene, 1,1,1,3,3-pentafluoropropane, 1,1,1,3,3-pentafluorobutane, heptafluorocyclopentane, and perfluorinated cyclic ethers (FLORINAT®). It is possible to use a mixture of at least two of these.

In the first process, it is optional to mix the poor solvent with a small amount of a good solvent in which solubility of 1,1,1,5,5,5-hexafluoroacetylacetone is higher than in the poor solvent. The amount of the good solvent may be not greater than 30 parts by weight per 100 parts by weight of the poor solvent. The good solvent in the invention is not particularly limited. Its examples are ethers such as diethyl ether, dibutyl ether, t-butyl methyl ether, diisopropyl ether, and tetrahydrofuran (THF); and alcohols such as methanol, ethanol, n-propanol, isopropanol, and n-butanol.

In the second process, it is optional to add a poor solvent to the solvent used for preparing the solution of the crude 1,1,1,5,5,5-hexafluoroacetylacetone dihydrate, in order to adjust the solubility in the solution. This addition is particularly preferable, if crystals of 1,1,1,5,5,5-hexafluoroacetylacetone are precipitated by lowering the temperature of the solution.

It is possible to dehydrate 1,1,1,5,5,5-hexafluoroacetylacetone dihydrate, which has been purified in accordance with the invention, by a conventional method, thereby obtaining its anhydride. R. Belford, J. Inorganic and Nuclear Chemistry, 1956, Vol. 2, pp. 11–31 discloses such method in which a dispersion is prepared by shaking 1,1,1,5,5,5-hexafluoroacetylacetone dihydrate with approximately three times its volume of 98% sulfuric acid. After the dispersion has been allowed to stand overnight, dehydration of the product is repeated with a fresh batch of sulfuric acid. The resulting upper layer is siphoned off and distilled, thereby obtaining the anhydride (yield: 98%) as a distillate between 70.0–70.2° C. J. Amer. Chem. Soc., 78, 2790 (1956) discloses another method in which anhydrous calcium sulfate is mixed with 1,1,1,5,5,5-hexafluoroacetylacetone dihydrate. Then, the resulting mixture is heated. The distillate is again treated with anhydrous calcium sulfate and distilled, thereby obtaining the anhydride of a boiling point of 68° C. (736 mm.). There is known a still another method in which 1,1,1,5,5,5-hexafluoroacetylacetone dihydrate, together with phosphorus pentoxide, is heated in ether.

The following nonlimiting examples are illustrative of the present invention.

EXAMPLE 1

Production of 1,1,1,5,5,5-Hexafluoroacetylacetone Dihydrate

A 500-ml three-necked flask, equipped with a thermometer, a dropping funnel and a reflux condenser, was charged with 34.6 g (0.64 mol) of sodium methoxide and 240 ml of t-butyl methyl ether. A mixture was prepared by mixing together 71.7 g (0.64 mol) of 1,1,1-trifluoroacetone, 90.9 g (0.64 mol) of ethyltrifluoroacetate, and 120 ml of t-butyl methyl ether. Then, the mixture was dropped into the flask by spending 30 min, while the reaction mixture was maintained at a temperature of not higher than 30° C. with stirring by a magnetic mixer. After the completion of the dropping, the reaction was conducted for 4 hr at 40° C. After the reaction, the reaction product was concentrated by distilling t-butyl methyl ether off using an evaporator, thereby obtaining a sodium salt of a crude 1,1,1,5,5,5-hexafluoroacetylacetone. This sodium salt was put into a 500-ml three-necked flask equipped with a thermometer and a reflux condenser. Then, 120 ml of water were added. Then, 160 g of 24% sulfuric acid aqueous solution were added at a temperature of not higher than 20° C. with stirring by a magnetic mixer. Then, the reaction was conducted for 6 hr at 60° C., followed by cooling to room temperature. The resulting reaction liquid was extracted with 200 ml of t-butyl methyl ether. The resulting water layer was again extracted with 100 ml of t-butyl methyl ether. The total of these organic layers was distilled with an evaporator to remove t-butyl methyl ether, thereby obtaining 118.8 g of a crude 1,1,1,5,5,5-hexafluoroacetylacetone dihydrate.

Production of 1,1,1,5,5,5-Hexafluoroacetylacetone

As shown in Table, 12 ml of toluene were added to 6.0 g of the obtained crude 1,1,1,5,5,5-hexafluoroacetylacetone dihydrate. The resulting mixture was stirred for 1 hr at room temperature with a magnetic mixer, followed by filtration and drying, thereby obtaining 5.3 g of 1,1,1,5,5,5-hexafluoroacetylacetone dihydrate. Then, a 20-ml eggplanttype flask was charged with 5.3 g of the obtained 1,1,1,5,5,5-hexafluoroacetylacetone dihydrate and 20 g of 98% sulfuric acid. Then, the flask was stopped, and the mixture was stirred for 4 hr at room temperature with a magnetic mixer, followed by standing still for 1 hr to have two layers separated from each other. Then, 4.0 g of 1,1,1,5,5,5-hexafluoroacetone were obtained from the organic layer. This product was found by a gas chromatography (detector: FID, column: DB-1, column size: 0.25 mm×60 m) to be 1,1,1,5,5,5-hexafluoroacetone having a purity of 99.9% (areal % in gas chromatography).

EXAMPLES 2-1–2-8

Production of 1,1,1,5,5,5-Hexafluoroacetylacetone

In each of Examples 2-1 to 2-8, the production of 1,1,1,5,5,5-hexafluoroacetylacetone of Example 1 was repeated except that a solvent shown in Table was added to 6.0 g of the crude 1,1,1,5,5,5-hexafluoroacetylacetone dihydrate obtained in Example 1. The results are shown in Table.

TABLE

|  | Solvent | Yield after Purification (g) | Yield after Dehydration (g) | Purity of 1,1,1,5,5,5-Hexafluoro-acetylacetone (areal %) |
|---|---|---|---|---|
| Example 1 | toluene 12 ml | 5.3 | 4.0 | 99.9 |
| Example 2-1 | n-hexane 12 ml | 5.4 | 4.1 | 99.8 |
| Example 2-2 | n-hexane 10 ml & t-butyl methyl ether 2 ml | 5.2 | 4.0 | 99.8 |
| Example 2-3 | n-hexane 10 ml & THF 2 ml | 4.2 | 3.2 | 99.9 |
| Example 2-4 | n-hexane 11 ml & methanol 2 ml | 5.0 | 3.8 | 99.7 |
| Example 2-5 | toluene 10 ml & THF 2 ml | 3.9 | 3.0 | 99.9 |
| Example 2-6 | toluene 10 ml & t-butyl methyl ether 2 ml | 4.8 | 3.7 | 99.9 |
| Example 2-7 | toluene 10 ml & dibutyl ether 2 ml | 5.3 | 4.1 | 99.9 |
| Example 2-8 | 1,3-bis(trifluoromethyl)benzene 12 ml | 5.1 | 3.9 | 99.8 |
| Example 3 | toluene 70 ml | 27.3 | 21.0 | 99.9 |
| Com. Ex. | No Solvent Treatment | 29.1 | 21.3 | 93.5 |

EXAMPLE 3

Production of 1,1,1,5,5,5-Hexafluoroacetylacetone Dihydrate

A 300-ml three-necked flask, equipped with a thermometer, a dropping funnel and a reflux condenser, was charged with 8.67 g (0.16 mol) of sodium methoxide and 60 ml of dibutyl ether. A mixture was prepared by mixing together 18.0 g (0.16 mol) of 1,1,1-trifluoroacetone, 22.8 g (0.16 mol) of ethyltrifluoroacetate, and 30 ml of dibutyl ether. Then, the mixture was dropped into the flask by spending 30 min, while the reaction mixture was maintained at a temperature of not higher than 30° C. with stirring by a magnetic mixer. After the completion of the dropping, the reaction was conducted for 4 hr at 40° C. After the reaction, the reaction product was concentrated by distilling dibutyl ether off with an evaporator, thereby obtaining a sodium salt of a crude 1,1,1,5,5,5-hexafluoroacetylacetone. This sodium salt was put into a 300-ml three-necked flask equipped with a thermometer and a reflux condenser. Then, 30 ml of water were added. Then, 40 g of 24% sulfuric acid aqueous solution were added at a temperature of not higher than 20° C. with stirring by a magnetic mixer. Then, the reaction was conducted for 6 hr at 60° C., followed by cooling to room temperature. The resulting reaction liquid was extracted with 50 ml of THF. The resulting water layer was again extracted with 40 ml of THF. The total of these organic layers was distilled with an evaporator to remove THF, thereby obtaining a crude 1,1,1,5,5,5-hexafluoroacetylacetone dihydrate.

Production of 1,1,1,5,5,5-Hexafluoroacetylacetone

To the obtained crude 1,1,1,5,5,5-hexafluoroacetylacetone dihydrate 70 ml of toluene were added, followed by stirring for 1 hr at room temperature with a magnetic mixer, then filtration and then drying, thereby obtaining 27.3 g of 1,1,1,,5,5,5-hexafluoroacetylacetone dihydrate (see Table). A 100-ml glass reaction vessel, equipped with a thermometer, a stirrer and a reflux condenser filled with glass spheres, was charged with 27.3 g of the obtained 1,1,1,5,5,5-hexafluoroacetylacetone dihydrate and 55 g of 98% sulfuric acid, while nitrogen gas was allowed to flow through the reaction vessel. Then, the mixture was gradually heated to 80° C. with stirring by a magnetic mixer. During this heating, 21.0 g of a distillate of about 70° C. was collected. This distillate was found by the same gas chromatography as that of Example 1 to be 1,1,1,5,5,5-hexafluoroacetylacetone having a purity of 99.9%.

COMPARATIVE EXAMPLE

Production of 1,1,1,5,5, 5-Hexafluoroacetylacetone

The production of 1,1,1,5,5,5-hexafluoroacetylacetone dihydrate of Example 3 was repeated, thereby obtaining 29.1 g of a crude 1,1,1,5,5,5-hexafluoroacetylacetone dihydrate.

Production of 1,1,1,5,5,5-Hexafluoroacetylacetone

A 100-ml glass reaction vessel, which is the same as that of Example 3, was charged with 29.1 g of the obtained crude 1,1,1,5,5,5-hexafluoroacetylacetone dihydrate and 58 g of 98% sulfuric acid. Then, the mixture was gradually heated to 80° C. with stirring by a magnetic mixer. During this heating, 21.3 g of a distillate of 70° C. was collected. This distillate was found by the same gas chromatography as that of Example 1 to be 1,1,1,5,5,5-hexafluoroacetylacetone having a purity of 93.5%.

The entire disclosure of Japanese Patent Application No. 2000-000526 filed on Jan. 5, 2000, including specification, claims and summary, is incorporated herein by reference in its entirety.

What is claimed is:

1. A process for producing 1,1,1,5,5,5-hexafluoroacetylacetone dihydrate, said process comprising:

reacting 1,1,1-trifluoroacetone with an ester of trifluoroacetic acid to prepare a crude 1,1,1,5,5,5-hexafluoroacetylacetone dihydrate containing an impurity; and bringing said cruse 1,1,1,5,5,5-hexafluoroacetylacetone dihydrate into contact with a poor solvent in which said 1,1,1,5,5,5-hexafluoroacetylacetone dihydrate is substantially insoluble, thereby removing said impurity from said crude 1,1,1,5,5,5-hexafluoroacetylacetone dihydrate.

2. A process according to claim 1, wherein said poor solvent has a boiling point of not higher than about 200° C.

3. A process according to claim 1, wherein said poor solvent is at least one selected from the group consisting of aromatic hydrocarbons, aliphatic hydrocarbons, alicyclic hydrocarbons, industrial gasolines, and fluorine-containing solvents.

4. A process according to claim 3, wherein said aromatic hydrocarbons are benzene, toluene, o-xylene, m-xylene, p-xylene, ethyl benzene, and mesitylene,
 wherein said aliphatic hydrocarbons are n-pentane, n-hexane, n-heptane, n-octane, n-nonane, n-decane, and isomers thereof, each of said isomers being in a liquid at about 5° C.,
 wherein said alicyclic hydrocarbons are cyclopentane, cyclohexane, methylcyclopentane, methylcyclohexane, tetralin, and decalin,
 wherein said industrial gasolines are ligroin and petroleum ether,
 wherein said fluorine-containing solvents are 1,2-bis(trifluoromethyl)benzene, 1,3-bis(trifluoromethyl)benzene, 1,4-bis(trifluoromethyl)benzene, 1,1,1,3,3-pentafluoropropane, 1,1,1,3,3-pentafluorobutane, heptafluorocyclopentane, and perfluorinated cyclic ethers.

5. A process according to claim 1, wherein said crude 1,1,1,5,5,5-hexafluoroacetylacetone dihydrate is brought into contact with a mixture of said poor solvent and a good solvent that is in an amount of not greater than 30 parts by weight per 100 parts by weight of said poor solvent, said good solvent being such that 1,1,1,5,5,5-hexafluoroacetylacetone dihydrate has a higher solubility in said good solvent than in said poor solvent.

6. A process according to claim 5, wherein said good solvent is at least one selected from the group consisting of ethers and alcohols.

7. A process according to claim 6, wherein each of said ethers has a boiling point of about 30–140° C.

8. A process according to claim 6, wherein said ethers are diethyl ether, dibutyl ether, t-butyl methyl ether, diisopropyl ether, and tetrahydrofuran.

9. A process according to claim 6, wherein said alcohols are methanol, ethanol, n-propanol, isopropanol, and n-butanol.

10. A process for producing 1,1,1,5,5,5-hexafluoroacetylacetone dihydrate, said process comprising:
 reacting 1,1,1-trifluoroacetone with an ester of trifluoroacetic acid to prepare a crude 1,1,1,5,5,5-hexafluoroacetylacetone dihydrate containing an impurity; and
 precipitating crystals of said 1,1,1,5,5,5-hexafluoroacetylacetone dihydrate from a solution of said crude 1,1,1,5,5,5-hexafluoroacetylacetone dihydrate.

11. A process according to claim 10, wherein said precipitating is conducted by adding a poor solvent, in which 1,1,1,5,5,5-hexafluoroacetylacetone is substantially insoluble, to said solution containing a good solvent in which 1,1,1,5,5,5-hexafluoroacetylacetone dihydrate has a higher solubility than in said poor solvent.

12. A process according to claim 11, wherein said poor solvent has a boiling point of not higher than about 200° C.

13. A process according to claim 11, wherein said poor solvent is at least one selected from the group consisting of aromatic hydrocarbons, aliphatic hydrocarbons, alicyclic hydrocarbons, industrial gasolines, and fluorine-containing solvents.

14. A process according to claim 13, wherein said aromatic hydrocarbons are benzene, toluene, o-xylene, m-xylene, p-xylene, ethyl benzene, and mesitylene,
 wherein said aliphatic hydrocarbons are n-pentane, n-hexane, n-heptane, n-octane, n-nonane, n-decane, and isomers thereof, each of said isomers being in a liquid at about 5° C.,
 wherein said alicyclic hydrocarbons are cyclopentane, cyclohexane, methylcyclopentane, methylcyclohexane, tetralin, and decalin,
 wherein said industrial gasolines are ligroin and petroleum ether,
 wherein said fluorine-containing solvents are 1,2-bis(trifluoromethyl)benzene, 1,3-bis(trifluoromethyl)benzene, 1,4-bis(trifluoromethyl)benzene, 1,1,1,3,3-pentafluoropropane, 1,1,1,3,3-pentafluorobutane, heptafluorocyclopentane, and perfluorinated cyclic ethers.

15. A process according to claim 11, wherein said good solvent is at least one selected from the group consisting of ethers and alcohols.

16. A process according to claim 15, wherein each of said ethers has a boiling point of about 30–140° C.

17. A process according to claim 15, wherein said ethers are diethyl ether, dibutyl ether, t-butyl methyl ether, diisopropyl ether, and tetrahydrofuran.

18. A process according to claim 15, wherein said alcohols are methanol, ethanol, n-propanol, isopropanol, and n-butanol.

19. A process according to claim 10, wherein said precipitating is conducted by lowering temperature of said solution.

20. A process according to claim 11, wherein said solution further contains an additional poor solvent in which 1,1,1,5,5,5-hexafluoroacetylacetone dihydrate is substantially insoluble.

* * * * *